United States Patent [19]

Marschner et al.

[11] Patent Number: 5,493,057
[45] Date of Patent: Feb. 20, 1996

[54] CHLOROETHYLSULFONYLBENZALDEHYDES

[75] Inventors: Claus Marschner, Speyer; Manfred Patsch, Wachenheim, both of Germany

[73] Assignee: BASF Aktiengesellschaft, Ludwigshafen, Germany

[21] Appl. No.: 57,830

[22] Filed: May 7, 1993

[30] Foreign Application Priority Data

May 20, 1992 [DE] Germany .......................... 42 16 590.3

[51] Int. Cl.$^6$ ................................................ C07C 317/14
[52] U.S. Cl. ................................................ 568/31; 568/30
[58] Field of Search ........................................ 568/30, 31

[56] References Cited

U.S. PATENT DOCUMENTS 4,922,014  5/1990  Papenfuhs .
5,055,605  10/1991  Ludvik ..................................... 568/31
5,082,976  1/1992  Blank et al. ............................. 568/30

Primary Examiner—José G. Dees
Assistant Examiner—Margaret Page
Attorney, Agent, or Firm—Oblon, Spivak, McClelland, Maier & Neustadt

[57] ABSTRACT

Chloroethylsulfonylbenzaldehydes of the formula

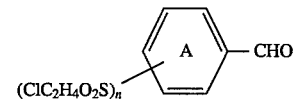

where
n is 1 or 2 and the ring A may be substituted with halogen, $C_1$–$C_4$alkyl, $C_1$–$C_4$alkoxy, $C_1$–$C_4$alkysulfonyl, nitro or hydroxysulfonyl, are prepared.

2 Claims, No Drawings

CHLOROETHYLSULFONYLBENZALDEHYDES

The present invention relates to novel chloroethylsulfonylbenzaldehydes of the formula I

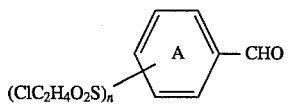

where
n is 1 or 2 and the ring A may be substituted, and to a process for preparing them.

It is an object of the present invention to provide novel advantageous intermediates for the synthesis of reactive dyes. The novel intermediates shall be preparable in a simple manner and in good yield.

We have found that this object is achieved by the chloroethylsulfonylbenzaldehydes of the formula I defined at the beginning.

In a substituted ring A in the formula I the substituents can be for example halogen, such as fluorine, chlorine, bromine or iodine, $C_1$–$C_4$-alkyl, such as methyl, ethyl, propyl, isopropyl, butyl, isobutyl or sec-butyl, $C_1$–$C_4$-alkoxy, such as methoxy, ethoxy, propoxy, isopropoxy, butoxy, isobutoxy or sec-butoxy, nitro, hydroxysulfonyl or $C_1$–$C_4$-alkylsulfonyl, such as methylsulfonyl, ethylsulfonyl, propylsulfonyl, isopropylsulfonyl or butylsufonyl. The number of substituents in a substituted ring A is in general from one to three, preferably one or two, in particular one.

U.S. Pat. No. 4,922,014 discloses the preparation of 2-hydroxymercaptobenzaldehydes. They are obtained by reacting halobenzaldehydes with 2-mercaptoethanol and can be converted into 2-hydroxyethylsulfonylbenzaldehydes by oxidation with hydrogen peroxide in the presence of tungsten compounds.

Preference is given to chloroethylsulfonylbenzaldehydes of the formula Ia or Ib

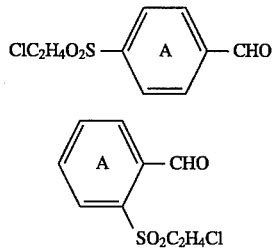

where the ring A is in either case as defined above.

Preference is further given to chloroethylsulfonylbenzaldehydes of the formula I where the ring A is unsubstituted or monosubstituted by halogen, by nitro or by hydroxysulfonyl.

The novel chloroethylsulfonylbenzaldehydes of the formula I can be obtained for example in an advantageous manner by oxidizing hydroxyethylmercaptobenzaldehydes of the formula II

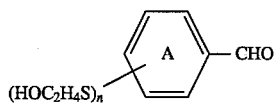

where n and the ring A are each as defined above, with elemental chlorine in hydrochloric acid solution at from 10° to 80° C., preferably at from 30° to 50° C.

Preference is given to a process wherein the oxidation is carried out in from 0.3 to 36% strength by weight, preferably from 18 to 36% strength by weight, hydrochloric acid.

The amount of hydrochloric acid used is in general from 0.5 to 5 parts by weight, preferably from 1 to 3 parts by weight, per part by weight of hydroxymercaptobenzaldehyde II.

The amount of elemental chlorine used is customarily from 2 to 6 mol, preferably from 2.5 to 4 mol, per mole of hydroxyethylmercaptobenzaldehyde II.

The novel process is advantageously carried out by preparing a solution of hydroxymercaptobenzaldehyde II in hydrochloric acid and introducing gaseous chlorine into it at the abovementioned temperature.

When the addition of chlorine is complete, which in general takes from 2 to 6 hours, the reaction mixture is subsequently stirred for about 3–4 hours. Then the resulting chloroethylsulfonylbenzaldehyde is filtered off with suction, washed with water and dried.

The starting hydroxymercaptobenzaldehydes are known per se and, as mentioned earlier, described for example in U.S. Pat. No. 4,922,014.

The novel process makes it possible to obtain the novel chloroethylsulfonylbenzaldehydes in high yield and high purity.

The novel chloroethylsulfonylbenzaldehydes of the formula I are useful intermediates for the synthesis of reactive dyes.

Embodiments of the invention will now be more particularly described by way of example.

EXAMPLE 1

91.0 g of 4-(2-hydroxyethyl)mercaptobenzaldehyde were dissolved in 160 g of concentrated hydrochloric acid. Chlorine was passed into the 35°–40° C. solution to the point of saturation, which took about 4 hours, and then the mixture was stirred at 35°–40° C. for 4 hours until starting material was no longer detectable by thin layer chromatography. Then the mixture was cooled with stirring to room temperature, and the suspended 4-(2-chloroethylsulfonyl)benzaldehyde was filtered off with suction, washed neutral with water and dried under reduced pressure at 40° C.

This produced 110 g of 4-(2-chloroethylsulfonyl)benzaldehyde of melting point 70°–72° C. (HPLC purity: 98%).

$Cl_{calc.}$: 15.27% $Cl_{obs.}$: 15.67%

$^1$H-NMR (DMSO): δ=3.8 (2H), 4.0 (2H), 8.1 (4H), 10.1 (1H) ppm.

EXAMPLE 2

Example 1 was repeated, except that the oxidation was carried out in 160 g of 0.4% strength by weight hydrochloric acid. This produced 105 g of 4-(2-chloroethylsulfonyl)benzaldehyde of similar purity.

EXAMPLE 3

Example 1 was repeated using a corresponding amount of 2-chloro-4-(2-hydroxyethylmercapto)benzaldehyde as starting material. This produced 2-chloro-4-(2-chloroethylsulfonyl)benzaldehyde in similar yield and purity.

$Cl_{calc.}$: 26.6% $Cl_{obs.}$: 25.73%

Melting point: 117°–119° C.

$^1$H-NMR (DMSO): δ=3.9 (2H), 4.1 (2H), 8.1 (2H), 8.2 (2H) 10.4 (1H) ppm.

The same method gives the benzaldehydes of the formula listed in the following table:

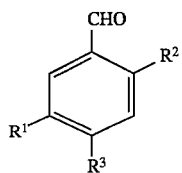

TABLE

| Example No. | R¹ | R² | R³ |
| --- | --- | --- | --- |
| 4 | H | SO₂CH₂CH₂Cl | H |
| 5 | H | SO₂CH₂CH₂Cl | SO₂CH₂CH₂Cl |
| 6 | Cl | H | SO₂CH₂CH₂Cl |
| 7 | Cl | SO₂CH₂CH₂Cl | SO₂CH₂CH₂Cl |
| 8 | Br | H | SO₂CH₂CH₂Cl |
| 9 | NO₂ | H | SO₂CH₂CH₂Cl |
| 10 | SO₃H | H | SO₂CH₂CH₂Cl |
| 11 | NO₂ | SO₂CH₂CH₂Cl | H |
| 12 | SO₃H | SO₂CH₂CH₂Cl | H |
| 13 | H | OCH₃ | SO₂CH₂CH₂Cl |

We claim:
1. Chloroethylsulfonylbenzaldehydes of the formula I

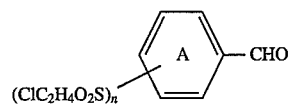

where
n is 1 or 2 and the ring A is optionally further substituted with halogen, $C_1$–$C_4$alkyl, $C_1$–$C_4$alkoxy, $C_1$–$C_4$alkylsulfonyl, nitro, or hydroxy sulfonyl.

2. Chloroethylsulfonylbenzaldehydes as claimed in claim 1 conforming to the formula Ia or Ib

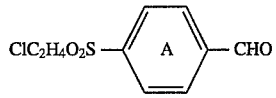

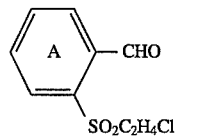

where the ring A is in either case as defined in claim 1.

* * * * *